US008209033B2

(12) United States Patent
Zhang et al.

(10) Patent No.: US 8,209,033 B2
(45) Date of Patent: Jun. 26, 2012

(54) METHOD AND APPARATUS FOR REGULATING BLOOD VOLUME USING VOLUME RECEPTOR STIMULATION

(75) Inventors: Yunlong Zhang, Mounds View, MN (US); James G. Bentsen, North St. Paul, MN (US); Yousufali Dalal, St. Louis Park, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 988 days.

(21) Appl. No.: 11/748,171

(22) Filed: May 14, 2007

(65) Prior Publication Data

US 2008/0288030 A1 Nov. 20, 2008

(51) Int. Cl.
*A61N 1/05* (2006.01)
(52) U.S. Cl. .......................... 607/120; 607/59; 607/116
(58) Field of Classification Search ................ 607/59, 607/9, 120, 115, 116, 62, 48, 24
See application file for complete search history.

(56) References Cited

U.S. PATENT DOCUMENTS

| 4,686,987 A | 8/1987 | Salo et al. |
| 4,791,931 A | 12/1988 | Slate |
| 5,042,497 A | 8/1991 | Shapland |
| 5,284,136 A | 2/1994 | Hauck et al. |
| 5,603,331 A | 2/1997 | Heemels et al. |
| 5,707,400 A | 1/1998 | Terry, Jr. et al. |
| 6,073,048 A | 6/2000 | Kieval et al. |
| 6,459,929 B1 | 10/2002 | Hopper et al. |
| 6,522,926 B1 | 2/2003 | Kieval et al. |
| 6,850,801 B2 | 2/2005 | Kieval et al. |
| 6,985,774 B2 | 1/2006 | Kieval et al. |
| 7,277,761 B2 | 10/2007 | Shelchuk |
| 2003/0216792 A1* | 11/2003 | Levin et al. ..................... 607/48 |
| 2005/0015129 A1* | 1/2005 | Mische ......................... 607/115 |
| 2005/0137626 A1 | 6/2005 | Pastore et al. |
| 2005/0149131 A1* | 7/2005 | Libbus et al. ..................... 607/9 |
| 2006/0217772 A1 | 9/2006 | Libbus et al. |
| 2006/0271116 A1 | 11/2006 | Stahmann et al. |
| 2007/0038259 A1 | 2/2007 | Kieval et al. |
| 2007/0038260 A1 | 2/2007 | Kieval et al. |
| 2007/0049989 A1* | 3/2007 | Rossing et al. ................. 607/59 |
| 2007/0255379 A1* | 11/2007 | Williams et al. .............. 607/120 |

FOREIGN PATENT DOCUMENTS

AU  2008253675 B2  11/2011

(Continued)

OTHER PUBLICATIONS

"International Application Serial No. PCT/US2008/006084, International Search Report mailed Nov. 6, 2008", 5 pgs.

(Continued)

*Primary Examiner* — Carl H. Layno
*Assistant Examiner* — Jon-Eric C. Morales
(74) *Attorney, Agent, or Firm* — Schwegman, Lundberg, Woessner, P.A.

(57) ABSTRACT

A system delivers stimulation to volume receptors in the cardiovascular system to induce diuresis in a patient suffering volume overload. The system senses a volume signal indicative of a level of fluid retention in the patient's body and controls the delivery of the stimulation using the volume signal. In various embodiments, the stimulation includes one or more of electrical stimulation, which delivers electrical pulses to the volume receptors, and mechanical stimulation, which physically stretches the volume receptors.

23 Claims, 8 Drawing Sheets

FOREIGN PATENT DOCUMENTS

| | | |
|---|---|---|
| JP | 2004-526471 A | 9/2004 |
| WO | WO-97/18856 A1 | 5/1997 |
| WO | WO-02/26314 A1 | 4/2002 |
| WO | WO-2007/092330 A1 | 8/2007 |
| WO | WO-2008/143832 A2 | 11/2008 |

OTHER PUBLICATIONS

"International Application Serial No. PCT/US2008/006084, Written Opinion mailed Nov. 6, 2008", 8 pgs.

"Australian Application Serial No. 2008253675, First Examiner Report mailed Aug. 16, 2010", 3 Pgs.

"Japanese Application Serial No. 2010-508395, Amended Claims filed Dec. 18, 2009", (w/ English Translation), 34 pgs.

"Australian Application Serial No. 2008253675, Response filed Jun. 17, 2011 to Examiner Report mailed Aug. 16, 2010", 15 pgs.

"Chinese Application Serial No. 200880015857.3, Office Action mailed May 18, 2011", 6 pgs.

"European Application Serial No. 08754391.4, Office Action mailed Apr. 29, 2011", 3 pgs.

"Chinese Application Serial No. 200880015857.3, Office Action Response mailed Oct. 21, 2011", 5 pgs.

"European Application Serial No. 08754391.4, Response filed Aug. 25, 2011 to Office Action dated Apr. 29, 2011", 16 pgs.

"Japanese Application Serial. No. 2010-508395, Office Action mailed Dec. 19, 2011", (w/ English Translation), 10 pgs.

* cited by examiner

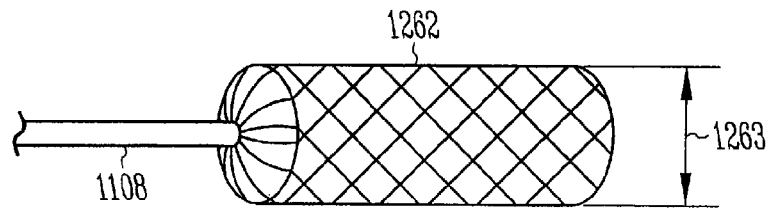
*Fig. 12*
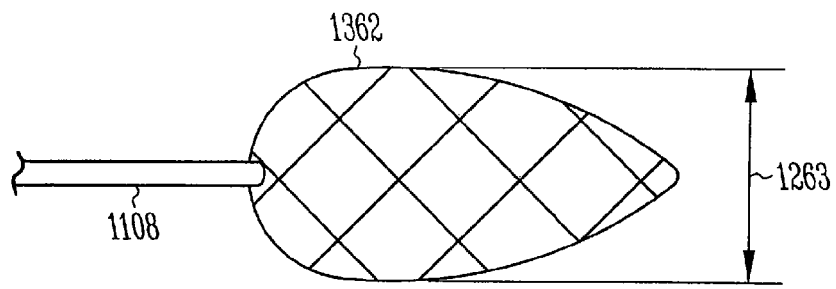
*Fig. 13*
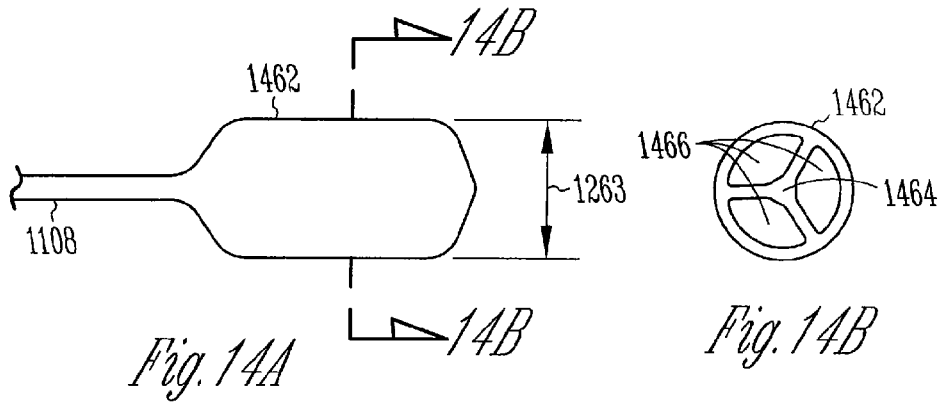
*Fig. 14A*  *Fig. 14B*
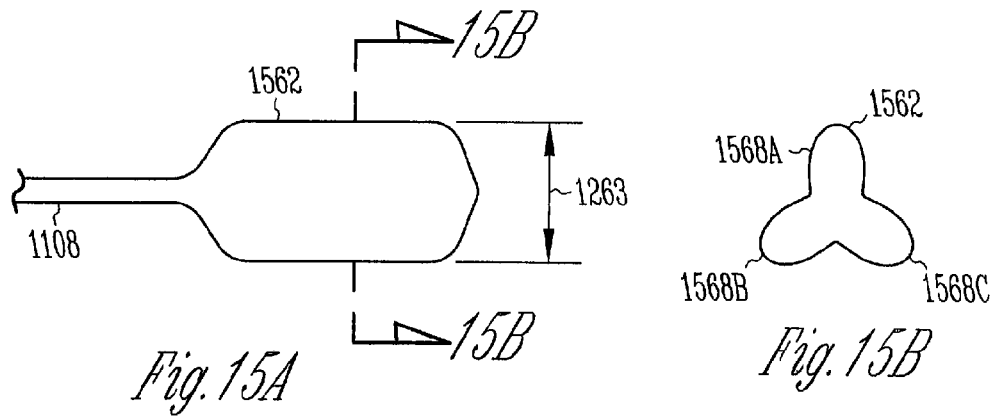
*Fig. 15A*  *Fig. 15B*

METHOD AND APPARATUS FOR REGULATING BLOOD VOLUME USING VOLUME RECEPTOR STIMULATION

TECHNICAL FIELD

This document relates generally to medical devices and particularly to an implantable system that regulates blood volume by stimulating volume receptors.

BACKGROUND

The heart is the center of a person's circulatory system. It includes an electro-mechanical system performing two major pumping functions. The left side of the heart, including the left atrium and left ventricle, draws oxygenated blood from the lungs and pumps it to various organs of the body to provide the organs with oxygen for their metabolic needs. This pumped blood flow is called the cardiac output. The right side of the heart, including the right atrium and right ventricle, draws deoxygenated blood from the organs and pumps it into the lungs where the blood gets oxygenated. The pumping functions are accomplished by contractions of the myocardium (heart muscles). In a normal heart, the sinoatrial node, the heart's natural pacemaker, generates electrical impulses, known as action potentials, that propagate through an electrical conduction system to various regions of the heart to excite myocardial tissues in these regions. Coordinated delays in the propagations of the action potentials in a normal electrical conduction system cause the various regions of the heart to contract in synchrony such that the pumping functions are performed efficiently.

Heart failure is a condition in which the myocardial muscle is weakened and its contractility is reduced, causing diminished cardiac output. A heart failure patient usually suffers from both a damaged electrical conduction system and a deteriorated myocardium. In response to the reduced cardiac output, the body attempts to adapt in a number of ways that lead to various symptoms as the heart failure condition progresses. A primary compensatory mechanism in heart failure includes increased sympathetic tone and an activated rennin-angiotensin system. This mechanism adversely reduces renal blood flow if the increased sympathetic tone and rennin-angiotensin activity persist. The body retains salt and water as a result of reduced renal blood flow. The salt and water are then accumulated in the lung and/or in peripheral tissues. Edema is caused by the increase of hydraulic pressure (reduction of oncotic pressure) in the circulation. The water retention may also lead to acute pulmonary edema, if the pulmonary capillary pressure reaches a certain level. In pulmonary edema, fluid leaks into the air sacs of the lung, causing the patient to gasp for breath. This condition can be fatal if not treated immediately. Another symptom of a patient with heart failure is fatigue on exertion. Once diagnosed with chronic heart failure, the patients is typically managed by interventions such as diet restriction and pharmacologic and/or device therapies. Such interventions keep the patient in a clinically stable state unless punctuated by episodes of acute heart failure decompensation. Acute heart failure decompensation is characterized by volume overload and shortness of breath, and requires immediate treatment in a hospital or an outpatient clinical setting.

Volume overload is the abnormally high blood volume resulting from fluid retention in the body including the circulatory system. A majority of hospitalization of heart failure patients is related to volume overload. Drug therapy has been applied to treat volume overload, thereby stopping or slowing the decompensation process. For example, diuretics are administrated orally (e.g., for decompensated heart failure) and intravenously (e.g., for acute decompensated heart failure) to restore fluid balance in the body. Because acute decompensated heart failure progresses rapidly after onset, a fast response upon early indications is needed.

SUMMARY

A system delivers stimulation to volume receptors in the cardiovascular system to induce diuresis in a patient suffering volume overload. The system senses a volume signal indicative of a level of fluid retention in the patient's body and controls the delivery of the stimulation using the volume signal. In various embodiments, the stimulation includes one or more of electrical stimulation, which delivers electrical pulses to the volume receptors, and mechanical stimulation, which physically stretches the volume receptors.

In one embodiment, a stimulation system includes a stimulation device, a fluid volume sensor, and a stimulation controller. The stimulation device delivers stimulation to the volume receptors. The fluid volume sensor senses a volume signal indicative of a level of fluid retention in the body. The stimulation controller controls the delivery of the stimulation using the volume signal and one or more parameters selected to induce diuresis.

In one embodiment, a method for regulating fluid volume in a body is provided. A volume signal indicative of a level of fluid retention in the body is sensed using a fluid volume sensor. Stimulation is delivered from a stimulation device to the volume receptors to induce diuresis. The delivery of the stimulation is controlled using the volume signal.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIG. 12 is an illustration of an embodiment of a dynamically adjustable stent of the mechanical stimulation device.

FIG. 13 is an illustration of an embodiment of a dynamically adjustable basket of the mechanical stimulation device.

FIGS. 14A-B are illustrations of an embodiment of a tubular balloon of the mechanical stimulation device.

FIGS. 15A-B are illustrations of an embodiment of a multi-lobe balloon of the mechanical stimulation device.

DETAILED DESCRIPTION

In the following detailed description, reference is made to the accompanying drawings which form a part hereof and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a system for stimulating certain types of baroreceptors in the cardiovascular system to induce diuresis as well as natriuresis in heart failure patients with volume overload. Baroreceptors include high pressure baroreceptors in arteries and low-pressure baroreceptors, known as volume receptors, in large veins and the heart. The high pressure baroreceptors sense blood pressure to allow for regulation of blood pressure and heart rate. Volume receptors sense blood volume to allow for regulation of fluid volume in the body. Normally, an increased volume of body fluid triggers and/or increases activities of the volume receptors by mechanical stretching. The increased activities of the volume receptors induce diuresis as well as natriuresis, thereby maintaining the body's balance of fluid intake and output. In heart failure patients with volume overload, the volume receptors are adapted to the condition and lose their sensitivity to the increased blood volume. The present system detects volume overload and in response, electrically and/or mechanically stimulate the volume receptors to induce diuresis, thereby restoring fluid balance in heart failure patients.

While electrical and mechanical stimulation of volume receptors are discussed in this document as specific examples, the electrical and mechanical stimulation system and method are applicable for stimulation of any type of baroreceptors in the cardiovascular system. In one embodiment, electrical and/or mechanical stimulation are delivered to stimulate the high pressure baroreceptors in one or more arteries to regulate hemodynamic conditions including blood pressure. In one embodiment, electrical and/or mechanical stimulation are delivered to stimulate the high pressure baroreceptors and the volume receptors in a coordinated manner to treat, for example, heart failure patients with volume overload and other symptoms.

Figure 1:
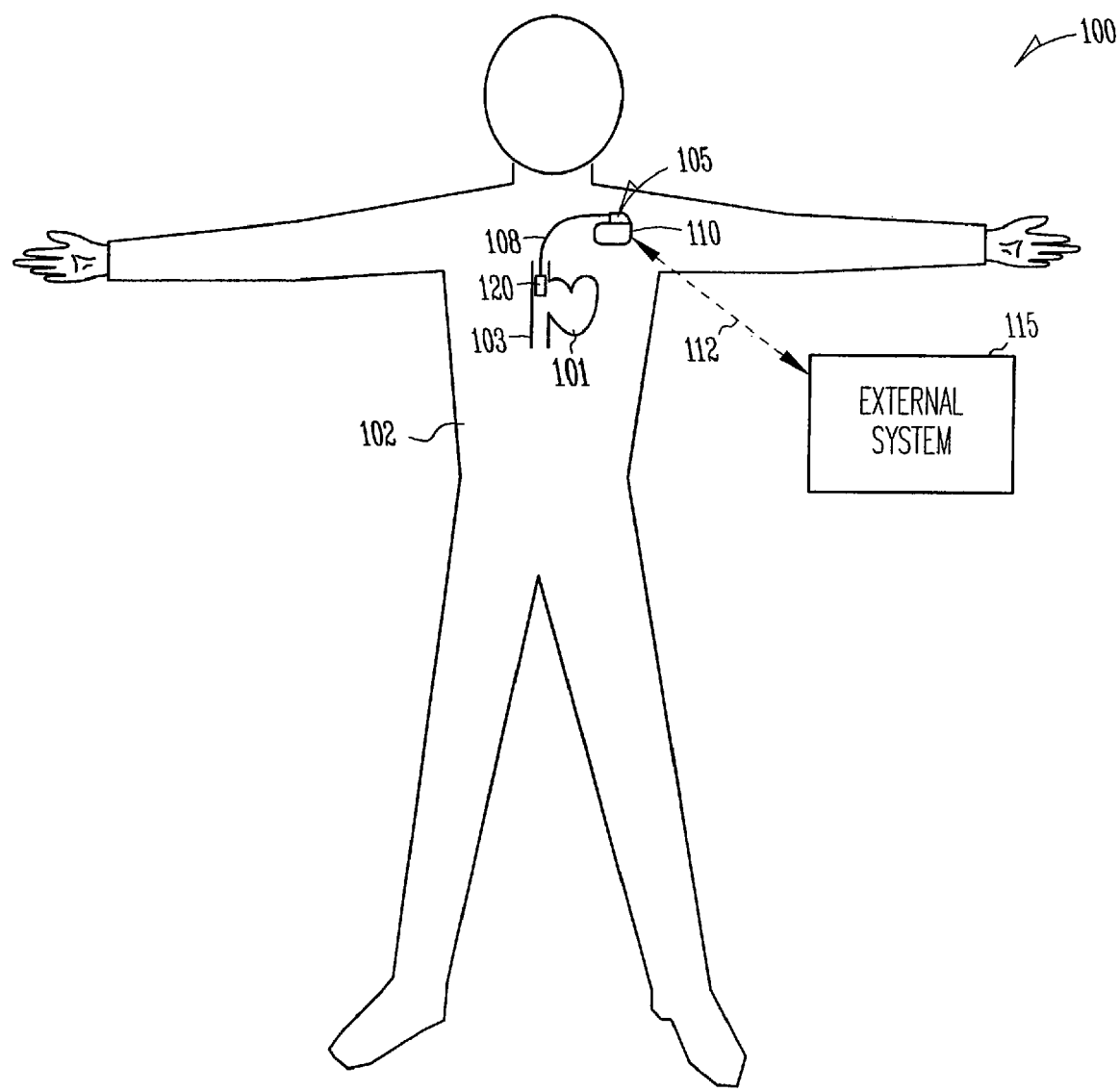
FIG. 1 is an illustration of an embodiment of a system for inducing diuresis and portions of an environment in which the system is used.

FIG. 1 is an illustration of an embodiment of a system 100 for inducing diuresis and portions of an environment in which system 100 is used. System 100 includes an implantable system 105, an external system 115, and a telemetry link 112 providing for communication between implantable system 105 and external system 115.

Implantable system 105 provides for stimulation of volume receptors to induce diuresis. In the illustrated embodiment, implantable system 105 includes an implantable medical device 110, a stimulator 120, and a lead system 108. Lead system 108 includes a lead connecting stimulator 120 to implantable medical device 110. In another embodiment, implantable system 105 includes an implantable medical device 110 and stimulator 120. Implantable medical device 110 and stimulator 120 are communicatively coupled via a wireless telemetry link. Stimulator 120 delivers electrical and/or mechanical stimulation to the volume receptors in a body 102. In one embodiment, implantable system 105 provides one or more therapeutic and/or monitoring functions in addition to the stimulation of the volume receptors. Implantable medical device 110 includes one or more of a physiological monitor, a pacemaker, a cardioverter/defibrillator, a cardiac resynchronization therapy (CRT) device, a cardiac remodeling control therapy (RCT) device, a neurostimulator, a drug delivery device or a drug delivery controller, and a biological therapy device. As illustrated in FIG. 1, implantable medical device 110 is implanted in body 102, and stimulator 120 is implanted in one or more portions of the cardiovascular system of body 102, such as in or near a junction of a vena cava 103 and a heart 101. In various embodiments, lead system 108 includes leads for stimulating the volume receptors as well as sensing physiological signals and delivering pacing pulses, cardioversion/defibrillation shocks, neurostimulation pulses, pharmaceutical agents, biological agents, and/or other types of energy or substance for treating cardiac disorders.

External system 115 allows a user such as a physician or other caregiver or a patient to control the operation of implantable medical device 110 and obtain information acquired by implantable medical device 110. In one embodiment, external system 115 includes a programmer communicating with implantable medical device 110 bi-directionally via telemetry link 112. In another embodiment, external system 115 is a patient management system including an external device communicating with a remote device through a telecommunication network. The external device is within the vicinity of implantable medical device 110 and communicates with implantable medical device 110 bi-directionally via telemetry link 112. The remote device allows the user to monitor and treat the patient from a distant location.

Telemetry link 112 provides for data transmission from implantable medical device 110 to external system 115. This includes, for example, transmitting real-time physiological data acquired by implantable medical device 110, extracting physiological data acquired by and stored in implantable medical device 110, extracting therapy history data stored in implantable medical device 110, and extracting data indicating an operational status of implantable medical device 110 (e.g., battery status and lead impedance). Telemetry link 112 also provides for data transmission from external system 115 to implantable medical device 110. This includes, for example, programming implantable medical device 110 to acquire physiological data, programming implantable medical device 110 to perform at least one self-diagnostic test (such as for a device operational status), and programming implantable medical device 110 to deliver at least one therapy.

Figure 2:
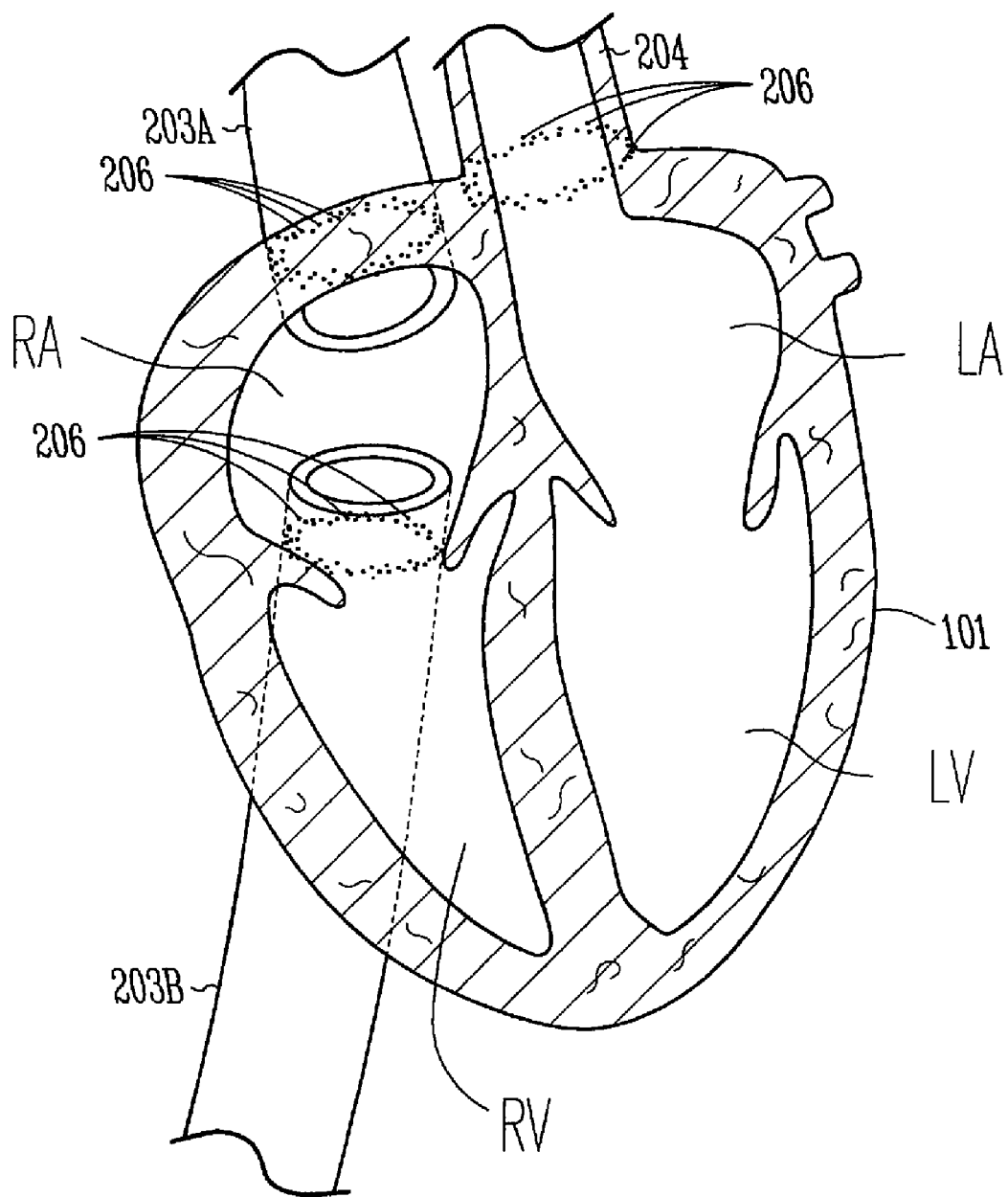
FIG. 2 is an illustration of locations of volume receptors in a cardiovascular system.

FIG. 2 is an illustration of locations of volume receptors 206 in a cardiovascular system. As shown in FIG. 2, heart 101 includes a right atrium (RA) connected to a superior vena cava 203A and an inferior vena cava 203B, and a left atrium (LA) connected to a pulmonary vein 204 (which represents one of the four pulmonary veins in a body for illustrative purposes only). Volume receptors are distributed in walls of the cardiovascular system in or near the junction of superior vena cava 203A and the RA, the junction of inferior vena cava 203B and the RA, and the junction of pulmonary vein 204 and the LA.

Figure 3:
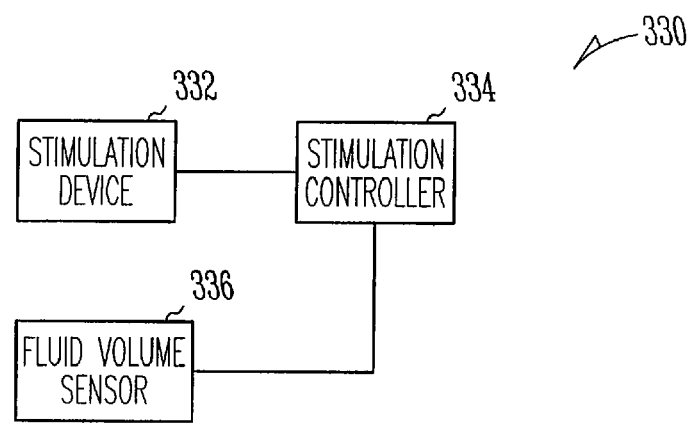
FIG. 3 is a block diagram illustrating an embodiment of a stimulation system.

FIG. 3 is a block diagram illustrating an embodiment of a stimulation system 330 for regulating fluid volume in body 102. Stimulation system 330 includes a stimulation device 332, a fluid volume sensor 336, and a stimulation controller 334. Stimulation device 332 delivers stimulation to the volume receptors in body 102. Fluid volume sensor 336 senses a volume signal indicative of a level of fluid retention in body 102. Stimulation controller 334 controls the delivery of the stimulation using the volume signal and one or more parameters selected to induce diuresis. In one embodiment, implantable system 105 includes stimulation system 330.

Figure 4:
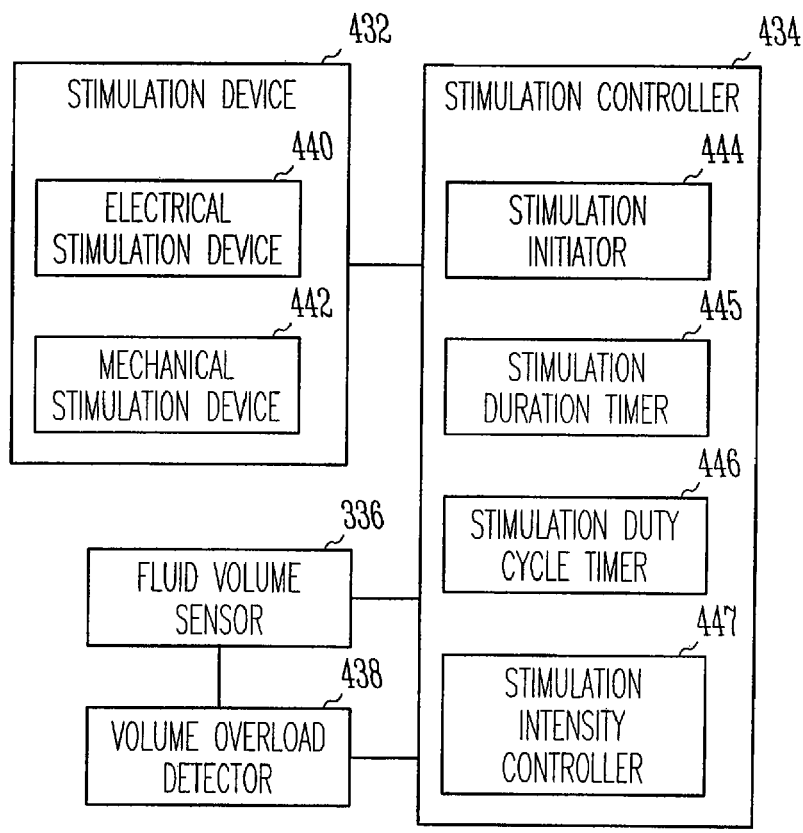
FIG. 4 is a block diagram illustrating another embodiment of the stimulation system.

FIG. 4 is a block diagram illustrating an embodiment of a stimulation system 430, which represents a specific embodiment of stimulation system 330. Stimulation system 430 includes a stimulation device 432, fluid volume sensor 336, a volume overload detector 438, and a stimulation controller 434.

Stimulation device 432 is an embodiment of stimulation device 332 and delivers stimulation to the volume receptors. In one embodiment, stimulation device 432 is configured to deliver the stimulation to the volume receptors in or near one or more of the junction of superior vena cava 203A and the RA, the junction of inferior vena cava 203B and the RA, and the junction of pulmonary vein 204 and the LA. The stimulation excites the volume receptors to induce diuresis. As illustrated in FIG. 4, stimulation device 432 includes an electrical stimulation device 440 and a mechanical stimulation device 442. In various embodiments, stimulation device 432 includes one or both of electrical stimulation device 440 and mechanical stimulation device 442. Electrical stimulation device 440 delivers electrical stimulation to the volume receptors. In one embodiment, the electrical stimulation includes electrical pulses capable of exciting the volume receptors by triggering action potentials. In one embodiment, the electrical stimulation also excites afferent neural pathways to effect systemic fluid regulation through the central nervous system. Mechanical stimulation device 442 delivers mechanical stimulation to the volume receptors. In one embodiment, the mechanical stimulation is capable of exciting the volume receptors by physically stretching them. Such mechanical stimulation more closely resembles the nature activation of the volume receptors than the electrical stimulation.

Fluid volume sensor 336 senses the volume signal. Volume overload detector 438 detects volume overload using the volume signal and a threshold. In one embodiment, volume overload detector 438 produces an alert signal when each occurrence of volume overload is detected.

The volume signal is used to indicate a level of fluid retention associated with heart failure. Heart failure results in diminished blood flow from the heart as measured by cardiac output or stroke volume. Cardiac output is the amount of blood pumped by the heart during a unit period of time. Stroke volume is the amount of blood pumped during each contraction or stroke. Decompensated heart failure occurs when the heart becomes significantly weakened such that the body's compensation mechanism cannot restore the normal cardiac output. One principal consequence of the decompensated heart failure is that the heart fails to provide the kidneys with sufficient blood to support normal renal function. As a result, volume overload occurs in most patients suffering decompensated heart failure. Thus, in various embodiments, one or more parameters indicative of body fluid volume and/or causes of decompensation are used to indicate volume overload.

In one embodiment, fluid volume sensor 336 includes an implantable impedance sensor to measure pulmonary impedance, or impedance of a portion of the thoracic cavity. Volume overload detector 438 detects the occurrence of volume overload when the impedance is out of its normal range. For example, pulmonary edema, i.e., fluid retention in the lungs resulting from the decreased cardiac output, decreases the pulmonary or thoracic impedance. In one specific embodiment, volume overload detector 438 detects the occurrence of volume overload when the pulmonary or thoracic impedance exceeds a predetermined threshold impedance. In one embodiment, the impedance sensor is a respiratory sensor that senses the patient's respiration rate and/or minute ventilation. An example of an impedance sensor for sensing respiratory activities is discussed in U.S. Pat. No. 6,459,929, "IMPLANTABLE CARDIAC RHYTHM MANAGEMENT DEVICE FOR ASSESSING STATUS OF CHF PATIENTS," assigned to Cardiac Pacemakers, Inc., which is incorporated herein by reference in its entirety.

In one embodiment, fluid volume sensor 336 includes a pressure sensor. Acute decompensated heart causes pressures in various portions of the cardiovascular system to deviate from their normal ranges. Volume overload detector 438 detects the occurrence of volume overload when a pressure is outside of its normal range. Examples of the pressure sensor include a left atrial (LA) pressure sensor, a left ventricular (LV) pressure sensor, a pulmonary artery pressure sensor, and a central venous pressure sensor. Elevated LA and pulmonary arterial pressures result in pulmonary edema. A deteriorated LV results in increased LV end diastolic pressure. In various embodiments, volume overload detector 438 detects the occurrence of volume overload when the LA pressure exceeds a predetermined threshold LA pressure level, when the pulmonary arterial pressure exceeds a predetermined threshold pulmonary arterial pressure level, and/or when the LV end diastolic pressure exceeds a predetermined threshold LV end diastolic pressure level. In other embodiments, volume overload detector 438 derives a parameter from one of these pressures, such as a rate of change of a pressure, and detects the occurrence of volume overload when the parameter deviates from its normal range. In one embodiment, the LV pressure sensor senses the LV pressure indirectly, by sensing a signal having known or predictable relationships with the LV pressure during all or a portion of the cardiac cycle. Examples of such a signal include an LA pressure and a coronary vein pressure. One specific example of measuring the LV pressure using a coronary vein pressure sensor is discussed in U.S. patent application Ser. No. 10/038,936, "METHOD AND APPARATUS FOR MEASURING LEFT VENTRICULAR PRESSURE," filed on Jan. 4, 2002, assigned to Cardiac Pacemakers, Inc., which is hereby incorporated by reference in its entirety.

In one embodiment, fluid volume sensor 336 includes a cardiac output or stroke volume sensor. Examples of stroke volume sensing are discussed in U.S. Pat. No. 4,686,987, "BIOMEDICAL METHOD AND APPARATUS FOR CONTROLLING THE ADMINISTRATION OF THERAPY TO A PATIENT IN RESPONSE TO CHANGES IN PHYSIOLOGIC DEMAND," and U.S. Pat. No. 5,284,136, "DUAL INDIFFERENT ELECTRODE PACEMAKER," both assigned to Cardiac Pacemakers, Inc., which are incorporated herein by reference in their entirety. Volume overload detector 438 detects the occurrence of volume overload when the cardiac output or stroke volume falls below a predetermined threshold level.

In one embodiment, fluid volume sensor 336 includes a neural activity sensor to detect activities of the sympathetic nerve and/or the parasympathetic nerve. A significant decrease in cardiac output immediately stimulates sympathetic activities, as the autonomic nervous system attempts to compensate for deteriorated cardiac function. Sympathetic activities sustain even when the compensation fails to restore the normal cardiac output. In one specific embodiment, the neural activity sensor includes a neurohormone sensor to sense a hormone level of the sympathetic nerve and/or the parasympathetic nerve. Volume overload detector 438 detects the occurrence of volume overload when the hormone level exceeds a predetermined threshold level. In another specific embodiment, the neural activity sensor includes an action potential recorder to sense the electrical activities in the sympathetic nerve and/or the parasympathetic nerve. Volume overload detector 438 detects the occurrence of volume overload when the frequency of the electrical activities in the sympathetic nerve exceeds a predetermined threshold level. Examples of direct and indirect neural activity sensing are discussed in U.S. Pat. No. 5,042,497, "ARRHYTHMIA PREDICTION AND PREVENTION FOR IMPLANTED DEVICES," assigned to Cardiac Pacemakers, Inc., which is hereby incorporated by reference in its entirety.

In one embodiment, fluid volume sensor 336 includes a renal function sensor. Acute decompensated heart failure results in peripheral edema primarily because of fluid retention of the kidneys that follows the reduction in cardiac output. The fluid retention is associated with reduced renal output, decreased glomerular filtration, and formation of angiotensin. Thus, in one specific embodiment, the renal function sensor includes a renal output sensor to sense a signal indicative of the renal output. Volume overload detector 438 detects the occurrence of volume overload when the sensed renal output falls below a predetermined threshold. In another specific embodiment, the renal function sensor includes a filtration rate sensor to sense a signal indicative of the glomerular filtration rate. Volume overload detector 438 detects the occurrence of volume overload when the sensed glomerular filtration rate falls below a predetermined threshold. In yet another specific embodiment, the renal function sensor includes a chemical sensor to sense a signal indicative of angiotensin II levels. Volume overload detector 438 detects the occurrence of volume overload when the sensed angiotensin II levels exceed a predetermined threshold level.

In one embodiment, fluid volume sensor 336 includes an acoustic sensor being a heart sound sensor and/or a respiratory sound sensor. Acute decompensated heart failure causes abnormal cardiac and pulmonary activity patterns and hence, deviation of heart sounds and respiratory sounds from their normal ranges of pattern and/or amplitude. Volume overload detector 438 detects the occurrence of volume overload when the heart sound or respiratory sound is out of its normal range. For example, detection of the third heard sound (S3) is known to indicate heart failure. In one specific embodiment, volume overload detector 438 detects the occurrence of volume overload when the S3 amplitude exceeds a predetermined threshold level.

In one embodiment, fluid volume sensor 336 includes a chemical sensor to sense one or more of blood concentration of atrial naturetic factor (ANF) and blood concentration of brain natriuretic factor (BNF). The blood concentrations of ANF and BNF are elevated due to volume overload. However, their diuresis and natriuresis effects are reduced due to the reduced renal blood flow and increased sympathetic and renin angiotensin system activities. Volume overload detector 438 detects the occurrence of volume overload when the blood concentration of ANF exceeds a predetermined threshold level and/or when the blood concentration of BNF exceeds a predetermined threshold level.

Embodiments of fluid volume sensor 336 are discussed in this document by way of example, but not by way of limitation. Other methods and sensors for sensing signals indicative of body fluid volume and level of fluid retention are useable as fluid volume sensor 438. In one embodiment, fluid volume sensor 336 includes two or more sensors to senses a plurality of signals indicative of a level of fluid retention in the patient's body. Volume overload detector 438 detects volume overload by applying a weighting factor to each of the sensed signals and comparing the sum of the weighted signals to a threshold.

Stimulation controller 434 is an embodiment of stimulation controller 334 and controls the delivery of the stimulation from stimulation device 432 using the volume signal. In one embodiment, stimulation controller 434 controls the delivery of the stimulation using one or more stimulation parameters such as a stimulation period at which the stimulation is initiated, a stimulation duration during which the stimulation is delivered, a stimulation duty cycle, and parameters controlling the intensity of the stimulation. In one embodiment, stimulation controller 434 adjusts the one or more stimulation parameters using feedback control with the volume signal as an input. In one embodiment, the one or more stimulation parameters are selected to induce diuresis while preventing desensitization of the volume receptors, such as by delivering intermittent stimulation at a reasonably low stimulation intensity. In the illustrated embodiment, stimulation controller 434 includes a stimulation initiator 444, a stimulation duration timer 445, a stimulation duty cycle timer 446, and a stimulation intensity controller 447. Stimulation initiator 444 initiates the delivery of stimulation using the stimulation period. In one embodiment, stimulation initiator 444 initiates the delivery of stimulation using the stimulation period in response to the detection of the volume overload. For example, in response to the alert signal produced by volume overload detector 438, stimulation initiator 444 initiates the delivery of stimulation on a periodic basis. In one embodiment, the stimulation is delivered on the period basis until the volume overload is no longer detected. Stimulation duration timer 445 times the delivery of stimulation using the stimulation duration following the initiation of the delivery of stimulation. Stimulation duty cycle timer 446 times the duty cycle, if programmed, during the stimulation duration. Stimulation intensity controller 447 controls the strength of stimulation. Examples of parameters controlling the intensity of in an electrical stimulation using electrical pulses include pulse frequency (or inter-pulse interval), pulse amplitude, and pulse width. Examples of parameters controlling the intensity of the mechanical stimulation using a cyclically expanding/contracting device include stimulation frequency (expanding/contracting cycle length) and degree of expansion/contraction (such as degree of volume change of a balloon). In one embodiment, stimulation controller 434 synchronizes the delivery of electrical pulses to cardiac events to prevent the volume receptor stimulation from causing unintended cardiac contraction. For example, the delivery of stimulation pulses to the volume receptors in or near the junction of superior vena cava 203A and the RA, and/or to the volume receptors in or near the junction of inferior vena cava 203B and the RA, are synchronized to the cardiac depolarization of the RA.

Similarly, the delivery of stimulation pulses to the volume receptors in or near the junction of pulmonary vein 204 and the LA, are synchronized to the cardiac depolarization of the LA.

In one embodiment, stimulation system 430 is distributed in implantable system 105. For example, implantable medical device 110 includes a hermetically sealed housing to house stimulation controller 434 and volume detector 438. Fluid volume sensor 336 is housed in or coupled to implantable medical device 110, depending on the type of sensor used. Stimulation device 432 is distributed in at least stimulator 120 but may also be distributed in lead system 108 and implantable medical device 110, as discussed below.

Figure 5:
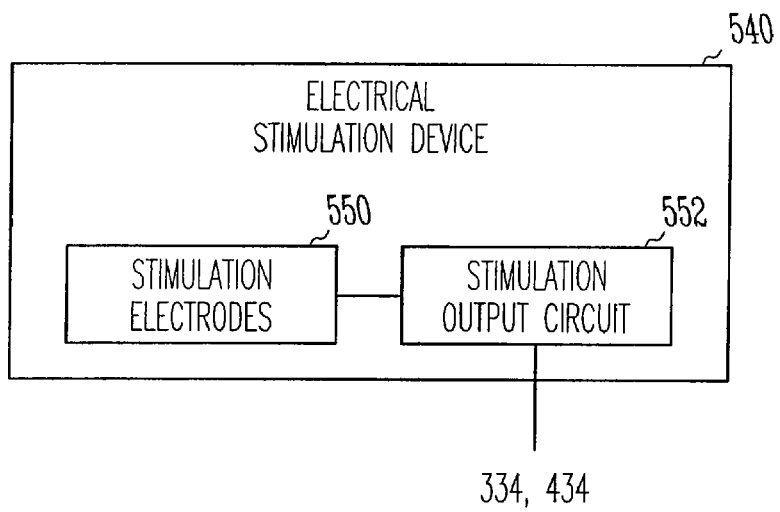
FIG. 5 is a block diagram illustrating an embodiment of an electrical stimulation device.

FIG. 5 is a block diagram illustrating an embodiment of an electrical stimulation device 540, which represents a specific embodiment of electrical stimulation device 440. Electrical stimulation device 540 includes stimulation electrodes 550 and a stimulation output circuit 552. Stimulation electrodes 550 are configured for delivering the electrical stimulation to the volume receptors. In one embodiment, at least one of the stimulation electrodes 550 is configured for intravascular placement in or near the junction of superior vena cava 203A and the RA, the junction of inferior vena cava 203B and the RA, or the junction of pulmonary vein 204 and the LA, such as being incorporated into a transvenous lead. In another embodiment, at least one of stimulation electrodes 550 is configured to brace a portion of the cardiovascular system in or near the junction of superior vena cava 203A and the RA, the junction of inferior vena cava 203B and the RA, or the junction of pulmonary vein 204 and the LA, such as being in the form of a cuff electrode. Stimulation output circuit 552 delivers the electrical stimulation through stimulation electrodes 550. In one embodiment, stimulation output circuit 552 generates electrical pulses.

Figure 6:
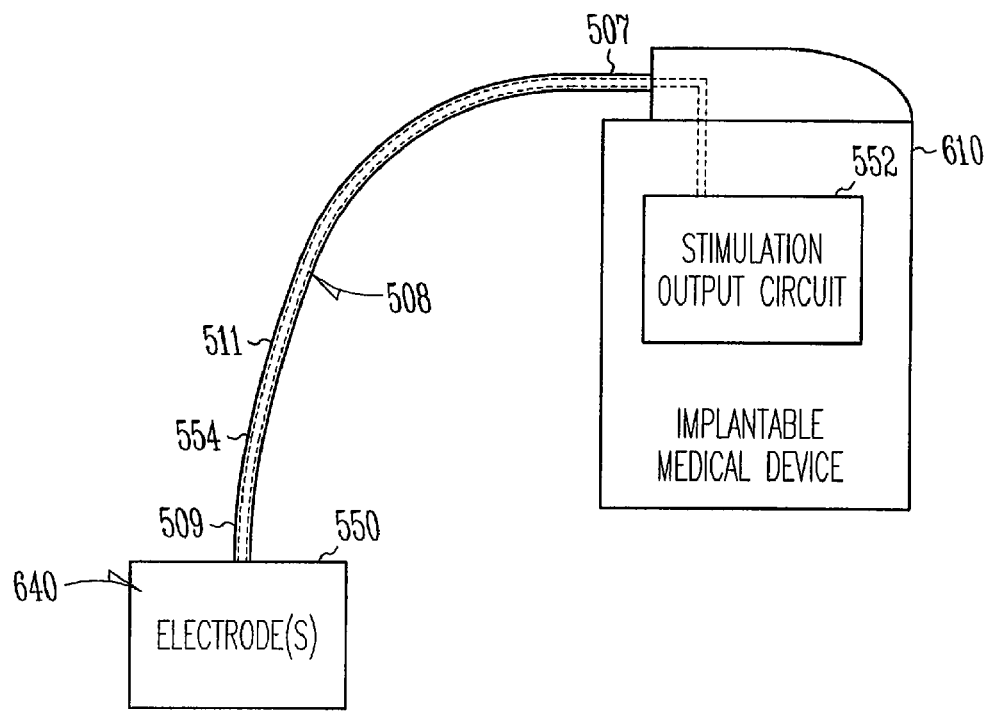
FIG. 6 is an illustration of an embodiment of an electrical stimulation device.

FIG. 6 is an illustration of an embodiment of an electrical stimulation device 640 and an implantable medical device 610. Implantable medical device 610 represents an embodiment of implantable medical device 110 and includes portions of electrical stimulation device 640. Electrical stimulation device 640 represents an embodiment of electrical stimulation device 540 and includes electrodes 550, stimulation output circuit 552, and an implantable lead 508. Implantable lead 508 includes a proximal end 507, a distal end 509, and an elongate body 511 coupled between proximal end 507 and distal end 509. Proximal end 507 is configured to be connected to implantable medical device 610. At least one of stimulation electrodes 550 is connected to distal end 509 or elsewhere along elongate body 511. In one embodiment, implantable lead 508 is a transvenous lead configured to allow intravascular placement of at least one of stimulation electrodes 550 near the volume receptors to deliver the electrical stimulation to the volume receptors. In another embodiment, implantable lead 508 is configured to allow at least one of stimulation electrodes 550 to be placed on the cardiovascular system over the volume receptors to deliver the electrical stimulation to the volume receptors. In one embodiment, one or more stimulation electrodes of stimulation electrodes 550 are incorporated onto implantable medical device 610. Stimulation output circuit 552 is housed in implantable medical device 610 and electrically connected to each electrode connected to implantable lead 508 using one or more conductors 554 extending within lead 508.

Figures 7, 8:
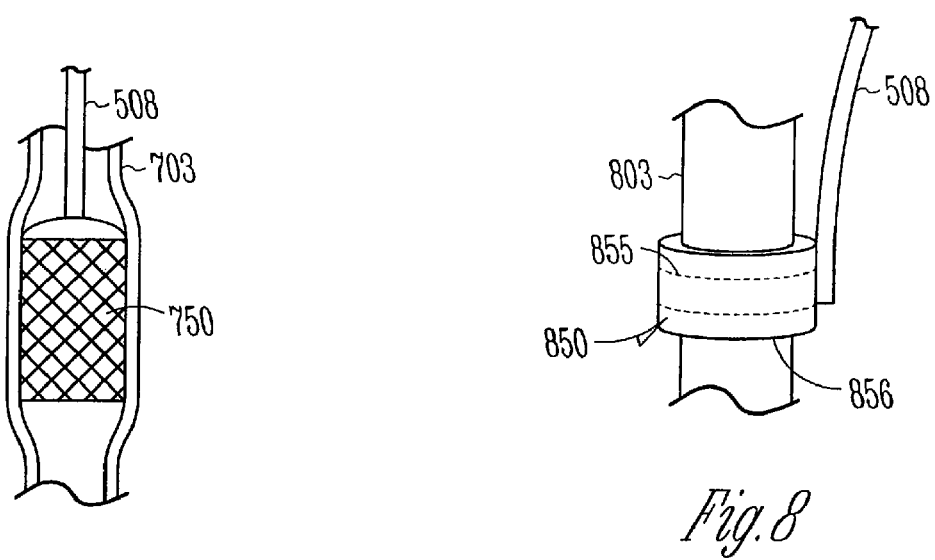
FIG. 7 is an illustration of an embodiment of a stent electrode of the electrical stimulation device.
FIG. 8 is an illustration of an embodiment of a cuff electrode of the electrical stimulation device.

FIG. 7 is an illustration of an embodiment of a stent electrode 750 as one of stimulation electrodes 550. Stent electrode 750 is in the form of an intravascular stent and connected to implantable lead 508. As illustrated in FIG. 7, stent electrode is placed in a portion of a blood vessel 703 where volume receptors are distributed. Examples of blood vessel 703 include superior vena cava 203A, inferior vena cava 203B, and pulmonary vein 204. In one embodiment, the intravascular stent is formed with a conductive mesh functioning as a stimulation electrode.

FIG. 8 is an illustration of another embodiment of a cuff electrode 850 as one of stimulation electrodes 550. Cuff electrode 850 is connected to lead 508 and includes a conductive element 855 functioning as a stimulation electrode and an electrode base (cuff) 856 configured to brace a portion of a blood vessel 803 where volume receptors are distributed. Examples of blood vessel 803 include superior vena cava 203A, inferior vena cava 203B, and pulmonary vein 204.

Figure 9:
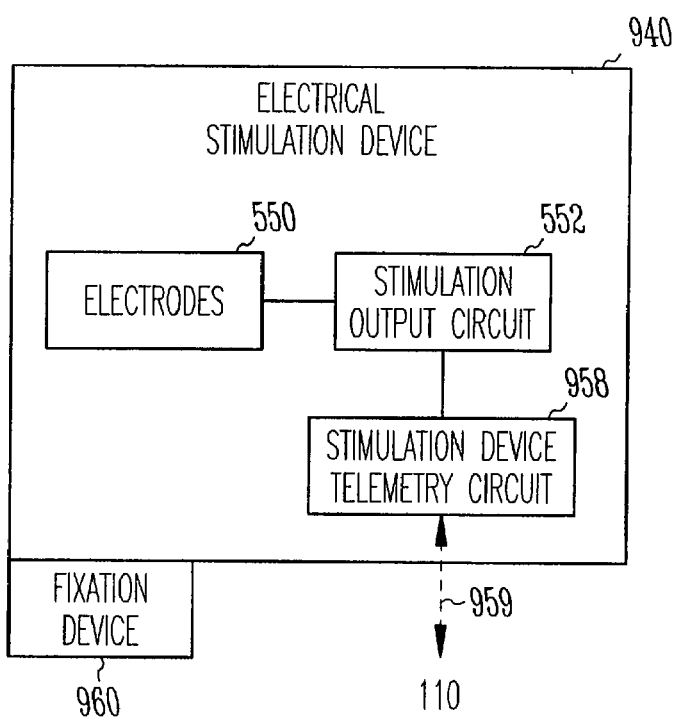
FIG. 9 is a block diagram illustrating another embodiment of the electrical stimulation device.

FIG. 9 is a block diagram illustrating an embodiment of an electrical stimulation device 940 connected to a fixation device 960. Electrical stimulation device 940 represents a specific embodiment of electrical stimulation device 440 and is wirelessly coupled to implantable medical device 110 and/or external system 115. Fixation device 960 stabilizes the position of electrical stimulation device 940 in the cardiovascular system after implantation. In one embodiment, electrical stimulation device 940 is to be placed in a blood vessel, and fixation device 960 includes a stent. In another embodiment, electrical stimulation device 940 is to be placed on a blood vessel, and fixation device 960 includes a bracing device such as a cuff.

Electrical stimulation device 940 includes electrodes 550, stimulation output circuit 552, and a stimulation device telemetry circuit 958. Stimulation device telemetry circuit 958 receives power and/or data from implantable medical device 110 and/or external system 115 via a telemetry link 959. Examples of telemetry link 959 includes a magnetic couple and an ultrasonic couple each capable of transmitting power and data across tissue.

Figure 10:
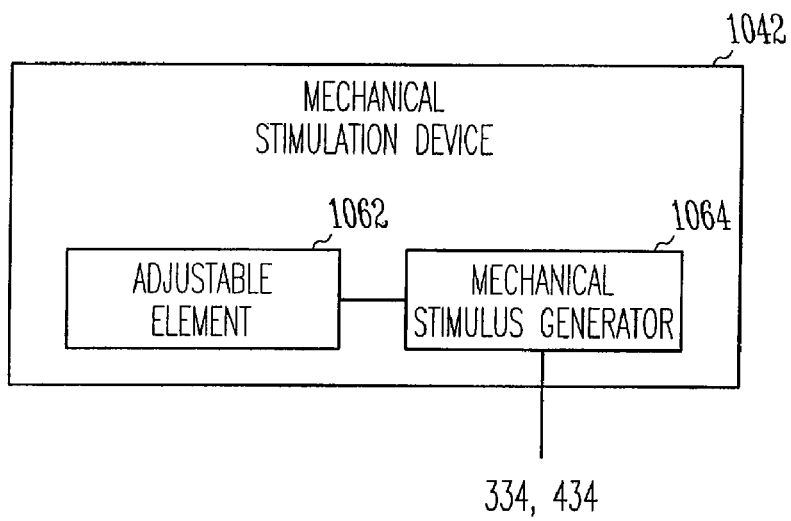
FIG. 10 is a block diagram illustrating an embodiment of a mechanical stimulation device.

FIG. 10 is a block diagram illustrating an embodiment of a mechanical stimulation device 1042, which represents a specific embodiment of mechanical stimulation device 442. Mechanical stimulation device 1042 includes an adjustable element 1062 and a mechanical stimulus generator 1064. Adjustable element 1062 is configured to be dynamically adjusted to stretch the volume receptors. Mechanical stimulus generator 1064 provides for the dynamic adjustment of adjustable element 1062. In one embodiment, adjustable element 1062 includes a diameter and/or volume that is electrically adjustable, and mechanical stimulus generator 1064 output an electrical current to cause expansion of the diameter and/or volume. In a specific embodiment, adjustable element 1062 includes a balloon filled with an electrically sensitive polymer gel that expands when an electrical current passes through. In another embodiment, adjustable element 1062 includes a balloon, and mechanical stimulus generator 1064 injects a fluid material to inflate the balloon and withdraws the fluid to deflate it.

Figure 11:
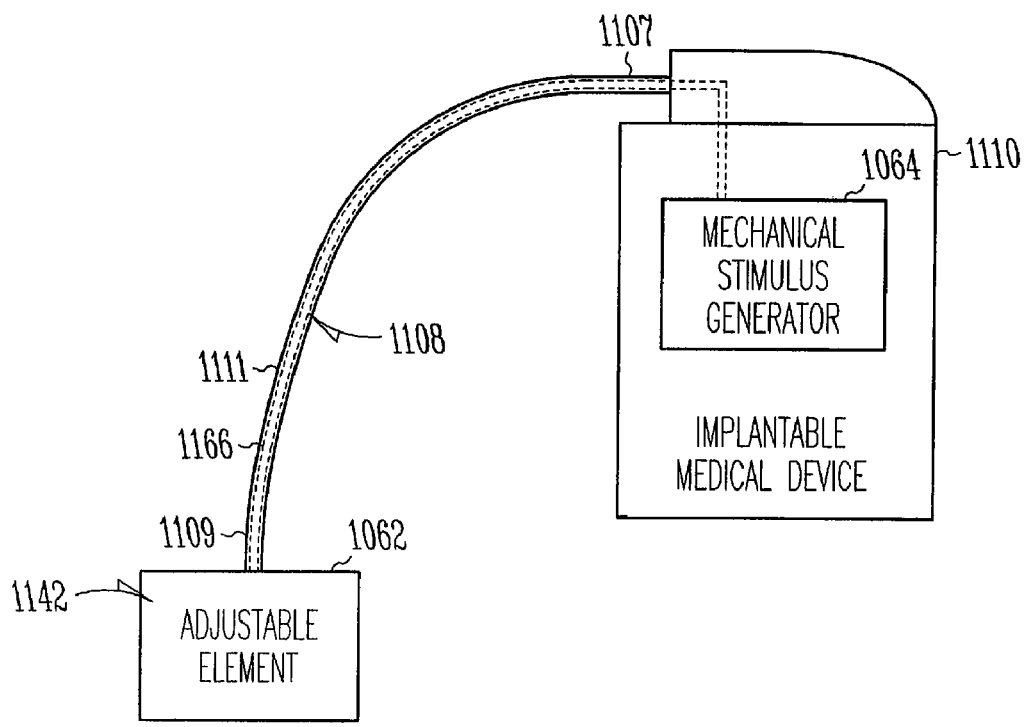
FIG. 11 is an illustration of an embodiment of a mechanical stimulation device.

FIG. 11 is an illustration of an embodiment of a mechanical stimulation device 1142 and an implantable medical device 1110. Implantable medical device 1110 represents an embodiment of implantable medical device 110 and includes portions of mechanical stimulation device 1142. Mechanical stimulation device 1142 represents an embodiment of mechanical stimulation device 1042 and includes adjustable element 1062, mechanical stimulus generator 1064, and an implantable lead 1108. Implantable lead 1108 includes a proximal end 1107, a distal end 1109, and an elongate body 1111 between proximal end 1107 and distal end 1109. Proximal end 1107 is configured to be connected to implantable medical device 1110. Adjustable element 1062 is connected to distal end 1109 or another location along elongate body 1111. Adjustable element 1062 and mechanical stimulus generator 1064 are coupled by a link 1166 extending within implantable lead 1108. In one embodiment, adjustable element 1062 is electrically adjustable and link 1166 includes electrical conductors. In another embodiment, adjustable element 1062 is adjusted using a fluid, and link 1166 includes a lumen to provide fluid communication between adjustable element 1062 (such as a balloon) and mechanical stimulus generator 1064 (such as a pump). In one embodiment, implantable lead 1108 is a transvenous lead configured to allow adjustable element 1062 to be placed in a blood vessel near the volume receptors. In another embodiment, implantable lead 1108 is configured to allow adjustable element 1062 to be placed on a portion of the vascular system over the volume receptors.

FIG. 12 is an illustration of an embodiment of a dynamically adjustable stent 1262, which is a specific embodiment of adjustable element 1062. Dynamically adjustable stent 1262 is configured for intravascular placement and has a dynamically adjustable diameter 1263. Dynamically adjustable diameter 1263 represents a diameter of an approximately cylindrical or tubular intravascular device placed in a blood vessel to stimulate the volume receptors when being expanded. In one embodiment, adjustable diameter 1263 is suitable for placing the approximately cylindrical or tubular intravascular device in superior vena cava 203A, inferior vena cava 203B, or pulmonary vein 204. In one embodiment, dynamically adjustable stent 1262 includes a mesh made of a material that is dynamically expandable, for example, by passing through an electrical current.

FIG. 13 is an illustration of an embodiment of a dynamically adjustable basket 1362, which is another specific embodiment of adjustable element 1062. Dynamically adjustable basket 1262 is configured for intravascular placement and has dynamically adjustable diameter 1263. In one embodiment, dynamically adjustable basket 1362 includes a net made of a material that is dynamically expandable, for example, by passing through an electrical current.

FIGS. 14A-B are illustrations of an embodiment of a tubular balloon 1462, which is another specific embodiment of adjustable element 1062. Tubular balloon 1462 is configured for intravascular placement and has dynamically adjustable diameter 1263. As illustrated in FIG. 14B, tubular balloon 1462 includes open spaces 1466 forming lumens between fluid passageways 1464. Fluid passageways 1464 allows inflation and deflation of tubular balloon 1462. Open spaces 1466 allow for substantially unobstructed flow of blood in a vessel after tubular balloon 1462 is placed in that vessel.

FIGS. 15A-B are illustrations of an embodiment of a multi-lobe balloon 1562, which is another specific embodiment of adjustable element 1062. Multi-lobe balloon 1562 is configured for intravascular placement and has dynamically adjustable diameter 1263. As illustrated in FIG. 15B, multi-lobe balloon 1562 includes lobes 1568A-C. The spaces between lobes 1568A-C allow for substantially unobstructed flow of blood in a vessel after multi-lobe balloon 1562 is placed in that vessel. In various embodiments, multi-lobe balloon 1562 includes any number lobes with any shapes suitable for the substantially unobstructed flow of blood.

Figure 16:
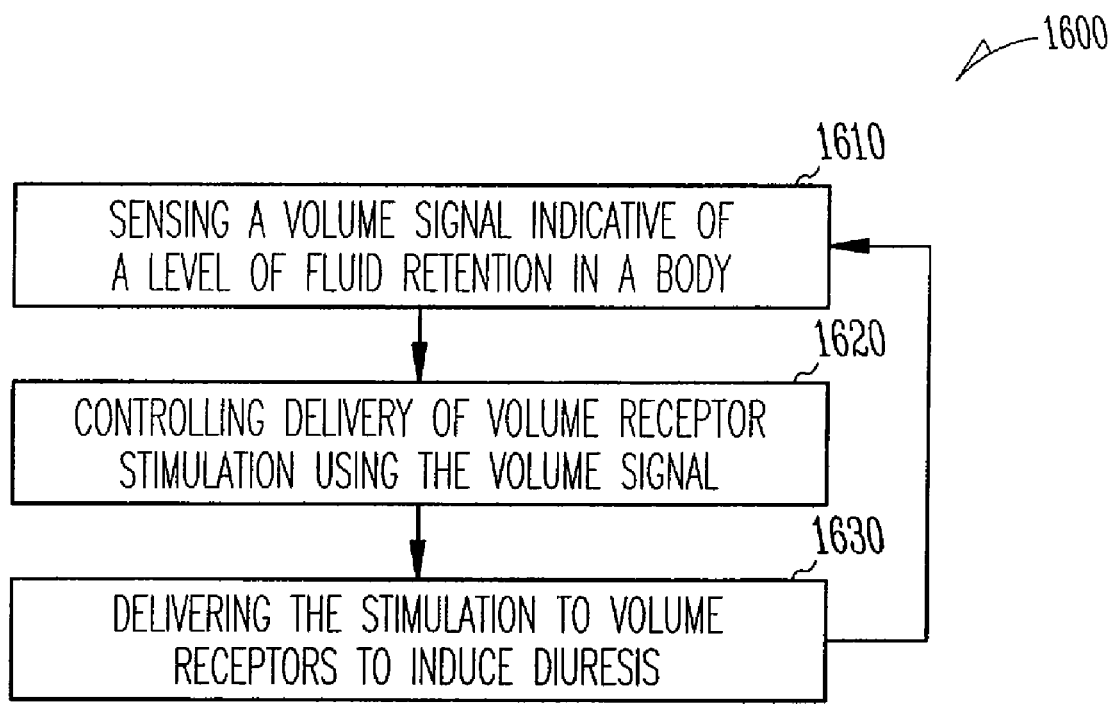
FIG. 16 is a flow chart illustrating a method for inducing diuresis by delivering stimulation.

FIG. 16 is a flow chart illustrating a method 1600 for inducing diuresis by delivering stimulation. In one embodiment, method 1600 is performed by system 100, including its various embodiments discussed above.

At 1610, a volume signal indicative of a level of fluid retention in a body is sensed. Examples of the volume signal include an impedance signal indicative of pulmonary or thoracic impedance, a pressure signal indicative of LA pressure, LV pressure, pulmonary artery pressure, or central venous pressure, a signal indicative of cardiac output or stroke volume, a neural signal indicative of activities of the sympathetic nerve and/or the parasympathetic nerve, a signal indicative of hormone level of the sympathetic nerve and/or the parasympathetic nerve, a signal indicative of renal function (renal output, glomerular filtration rate, or angiotensin II level), a heart sounds signal, and a signal indicative of blood concentration of ANF and/or blood concentration of BNF. In various embodiments, any one or more signals that indicate body fluid volume and allow for monitoring of volume overload are sensed at 1610. In one embodiment, occurrences of the volume overload are detected using the volume signal and a threshold. In one embodiment, a plurality of signals that indicate body fluid volume and allow for monitoring of volume overload are sensed, and occurrences of the volume overload are detected by applying different weighting factors to the signals. For example, the impedance signal, the pressure signal indicative of LA pressure, LV pressure, pulmonary artery pressure, or central venous pressure, the signal indicative of cardiac output or stroke volume, and the heart sound signal are given higher weight than the neural signal indicative of activities of the sympathetic nerve and/or the parasympathetic nerve, the signal indicative of hormone level of the sympathetic nerve and/or the parasympathetic nerve, the signal indicative of renal function, and the signal indicative of blood concentration of ANF and/or blood concentration of BNF. In a further embodiment, an alert signal is produced in response to the detection of an occurrence of the volume overload.

At 1620, delivery of volume receptor stimulation is controlled using the volume signal. In one embodiment, the stimulation is initiated in response to the detection of an occurrence of the volume overload. In one embodiment, the volume receptor stimulation is controlled using one or more stimulation parameters that are adjusted using feedback control with the volume signal as an input. Examples of the stimulation parameters include a stimulation period at which the stimulation is initiated, a stimulation duration during which the stimulation is delivered, a stimulation duty cycle, and parameters controlling the intensity of the stimulation. In one embodiment, the stimulation is initiated using a stimulation period and the volume signal. For example, after the stimulation is first initiated in response to the detection of an occurrence of the volume overload, it is repeated on a periodic basis until the volume overload is no longer detected. Following the initiation, the delivery of the stimulation is timed using the stimulation duration. In one embodiment, a duty cycle is timed to allow intermittent delivery of the stimulation during the stimulation duration. In various embodiments, the timing and intensity of the stimulation are controlled to induce diuresis while minimizing potential desensitization of the volume receptors.

At 1630, the stimulation is delivered to the volume receptors to induce diuresis. In various embodiments, the stimulation is delivered to one or more regions in the cardiovascular system in or near the junction of superior vena cava and right atrium, the junction of inferior vena cava and right atrium, and the junction of pulmonary vein and left atrium. In various embodiments, the stimulation includes one or more of electrical stimulation and mechanical stimulation. In one embodiment, the electrical stimulation includes delivering electrical pulses using one or more electrodes placed in or on a portion of the cardiovascular system over the volume receptors. The electrical pulses elicit action potentials in the volume receptors. In one embodiment, the mechanical stimulation includes stretching the volume receptors using a stimulation device with a dynamically adjustable dimension or volume. The stimulation device is placed in a vessel or braces the vessel. Examples of such stimulation device include dynamically adjustable intravascular stent or basket, a balloon for intravascular placement, and a ring-shaped balloon to brace a blood vessel. The balloon for intravascular placement includes open spaces or lumens to allow for substantially unobstructed blood flow in the vessel in which the balloon is placed.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A stimulation system for regulating fluid volume in a body having a cardiovascular system including a superior vena cava, an inferior vena cava, a pulmonary vein, a right atrium, and a left atrium by stimulating volume receptors distributed in the cardiovascular system in or near one or more of a junction of the superior vena and the right atrium, a junction of the inferior vena cava and the right atrium, and a junction of the pulmonary vein and the left atrium, the volume receptors being low-pressure baroreceptors sensing blood volume in the body, the system comprising:
    a stimulation device configured to deliver stimulation to the volume receptors;
    a fluid volume sensor configured to sense a volume signal indicative of a level of fluid retention in the body; and
    a stimulation controller coupled to the stimulation device and the fluid volume sensor, the stimulation controller programmed to control the delivery of the stimulation using the volume signal and one or more stimulation parameters selected to induce diuresis while preventing desensitization of the volume receptors.

2. The system of claim 1, comprising a volume overload detector adapted to detect volume overload using the volume signal and a threshold, and wherein the stimulation controller is programmed to initiate the delivery of the stimulation in response to the detection of the volume overload.

3. The system of claim 1, wherein the stimulation controller is programmed to adjust the one or more stimulation parameters using feedback control with the volume signal being an input.

4. The system of claim 1, wherein the stimulation controller comprises a stimulation initiator programmed to initiate the delivery of the stimulation using one or more of the volume signal and a stimulation period.

5. The system of claim 4, wherein the stimulation controller further comprises one or more of a stimulation duration timer and a stimulation duty cycle timer, the stimulation duration timer programmed to time the delivery of stimulation using the stimulation duration following the initiation of the delivery of stimulation, the stimulation duty cycle timer programmed to time a duty cycle during the stimulation duration.

6. The system of claim 1, wherein the stimulation device comprises an electrical stimulation device including
    stimulation electrodes configured to deliver electrical stimulation to the volume receptors; and
    a stimulation output circuit configured to deliver the electrical stimulation through the electrodes.

7. The system of claim 6, comprising an implantable medical device including at least the stimulation controller, and wherein the electrical stimulation device is wirelessly coupled to the implantable medical device and comprises a fixation device to stabilize a position of the electrical stimulation device in the cardiovascular system.

8. The system of claim 6, comprising:
    an implantable medical device including at least the stimulation controller; and
    an implantable transvenous lead including a proximal end, a distal end, and an elongate body between the proximal end and the distal end, the proximal end configured to be connected to the implantable medical device,
    wherein at least one of the stimulation electrodes is connected to the distal end, and the implantable transvenous lead is configured to allow intravascular placement of the at least one of the stimulation electrodes.

9. The system of claim 6, comprising:
    an implantable medical device including at least the stimulation controller; and
    an implantable lead including a proximal end, a distal end, and an elongate body between the proximal end and the distal end, the proximal end configured to be connected to the implantable medical device,
    wherein at least one of the stimulation electrodes is connected to the distal end, and wherein the implantable lead is configured to allow the at least one of the stimulation electrodes to be placed on the cardiovascular system over the volume receptors.

10. The system of claim 1, wherein the stimulation device comprises a mechanical stimulation device including:
    an adjustable element configured to stretch the volume receptors when being adjusted; and
    a mechanical stimulus generator to adjust the adjustable element.

11. The system of claim 10, comprising:
    an implantable medical device including at least the stimulation controller and the mechanical stimulus generator; and
    an implantable transvenous lead including a proximal end, a distal end, and an elongate body between the proximal end and the distal end, the proximal end configured to be connected to the implantable medical device,
    wherein the adjustable element is connected to the distal end, and the implantable transvenous lead is configured to allow intravascular placement of the adjustable element to stretch the volume receptors.

12. The system of claim 1, wherein the fluid volume sensor comprises a chemical sensor configured to sense one or more of blood concentration of atrial naturetic factor (ANF) and blood concentration of brain naturetic factor (BNF).

13. The system of claim 2, wherein the fluid volume sensor comprises a plurality of sensors configured to sense a plurality of signals indicative of the level of fluid retention in the body, and the volume overload detector is configured to detect the volume overload by using the sensed plurality of signals, weighting factors each to be applied to a signal of the sensed plurality of signals, and a threshold.

14. The system of claim 6, wherein the stimulation output circuit is configured to deliver electrical stimulation pulses through the electrodes to the volume receptors, and the stimulation controller is configured to synchronize the delivery of the electrical stimulation pulses to cardiac depolarization.

15. A method for regulating fluid volume in a body having a cardiovascular system including a superior vena cava, an inferior vena cava, a pulmonary vein, a right atrium, and a left atrium, the method comprising:
    sensing a volume signal indicative of a level of fluid retention in the body using a fluid volume sensor;

delivering stimulation from a stimulation device to volume receptors distributed in the cardiovascular system in or near one or more of a junction of the superior vena and the right atrium, a junction of the inferior vena cava and the right atrium, and a junction of the pulmonary vein and the left atrium to induce diuresis while preventing desensitization of the volume receptors, the volume receptors being low-pressure baroreceptors sensing blood volume in the body; and controlling the delivery of the stimulation using the volume signal.

16. The method of claim 15, wherein delivering stimulation from the stimulation device to the volume receptors comprises delivering electrical pulses from an electrical stimulation device to the volume receptors.

17. The method of claim 15, wherein delivering stimulation to the volume receptors comprises mechanically stretching the volume receptors using a mechanical stimulation device.

18. The method of claim 15, comprising detecting an occurrence of volume overload using the volume signal and a threshold, and wherein delivering the stimulation comprises delivering the stimulation in response to the detection of the occurrence of volume overload.

19. The method of claim 18, wherein delivering the stimulation comprises adjusting one or more stimulation parameters using feedback control using the volume signal as an input.

20. The method of claim 15, wherein controlling the delivery of the stimulation comprises initiating the delivery of the stimulation using a stimulation period and the volume signal.

21. The method of claim 20, wherein controlling the delivery of the stimulation comprises timing the delivery of stimulation using a stimulation duration following the initiation of the delivery of stimulation.

22. The method of claim 21, wherein controlling the delivery of the stimulation comprises timing a duty cycle during the stimulation duration.

23. A method for regulating fluid volume in a body having volume receptors in a cardiovascular system, the method comprising:

sensing a plurality of signals each indicative of a level of fluid retention in the body using a fluid volume sensor;

detecting an occurrence of volume overload using the plurality of signals, weighting factors each applied to a signal of the plurality of signals, and a threshold; and delivering stimulation from a stimulation device to the volume receptors to induce diuresis in response to the detection of the occurrence of volume overload.

* * * * *